United States Patent
Guerin-Deremaux et al.

(10) Patent No.: US 8,871,740 B2
(45) Date of Patent: Oct. 28, 2014

(54) USE OF POLYSACCHARIDES FOR TREATING STRESS AND ANXIETY

(75) Inventors: Laetitia Guerin-Deremaux, Nieppe (FR); Daniel Wils, Morbecque (FR)

(73) Assignee: Roquette Freres, Lestrem (FR)

(*) Notice: Subject to any disclaimer, the term of this patent is extended or adjusted under 35 U.S.C. 154(b) by 5 days.

(21) Appl. No.: 13/519,006

(22) PCT Filed: Dec. 23, 2010

(86) PCT No.: PCT/FR2010/052911
§ 371 (c)(1),
(2), (4) Date: Jun. 25, 2012

(87) PCT Pub. No.: WO2011/077063
PCT Pub. Date: Jun. 30, 2011

(65) Prior Publication Data
US 2012/0283212 A1    Nov. 8, 2012

(30) Foreign Application Priority Data

Dec. 24, 2009 (FR) ..................... 09 59605

(51) Int. Cl.
*A61K 31/715* (2006.01)
*A61K 31/718* (2006.01)
*A61K 45/06* (2006.01)
*A61K 31/55* (2006.01)

(52) U.S. Cl.
CPC ............. *A61K 45/06* (2013.01); *A61K 31/55* (2013.01); *A61K 31/715* (2013.01); *A61K 31/718* (2013.01)
USPC ............. 514/54; 514/58; 536/123.1; 536/103

(58) Field of Classification Search
USPC ..................... 514/54, 58; 536/123.1, 103
See application file for complete search history.

(56) References Cited

U.S. PATENT DOCUMENTS

| | | | |
|---|---|---|---|
| 5,760,014 | A | 6/1998 | Wurtman et al. |
| 2006/0084629 | A1 | 4/2006 | Needleman et al. |
| 2006/0147569 | A1 | 7/2006 | Kung et al. |

FOREIGN PATENT DOCUMENTS

| | | | |
|---|---|---|---|
| CN | 1876003 | A | 12/2006 |
| CN | 101077357 | A | 11/2007 |
| EP | 1006128 | A1 | 6/2000 |
| EP | 2179727 | A1 | 4/2010 |
| FR | 2846518 | * | 5/2004 |
| WO | 02074104 | A1 | 9/2002 |
| WO | 2007058923 | A2 | 5/2007 |

OTHER PUBLICATIONS

Serpelloni; FR 2846518; May 7, 2004 (English Machine Translation).*
Fouache et al.; EP1006128 A1; Jun. 7, 2000 (English Machine Translation).*
Li Yun Feng et al., "Inhibition of the oligosaccharides extracted from *Morinda officinalis*, a Chinese traditional herbal medicine, on the corticosterone induced apoptosis in PC12 cells", Life Sciences 72 (2003) 933-942, XP-002585872.
International Search Report dated Mar. 22, 2011, from corresponding PCT application.

* cited by examiner

*Primary Examiner* — Layla Bland
*Assistant Examiner* — Michael C Henry
(74) *Attorney, Agent, or Firm* — Young & Thompson

(57) ABSTRACT

The present invention relates to a composition including a mix of a polysaccharides having: 15% to 50% of glucoside linkages 1-6; a reducing sugar content of less than 20%; a polymolecularity index of less than 5; an average molecular weight with number Mn of less than 4500 g/mole and at least one active agent for treating stress, anxiety and depressive behavior, sleep disorders, obsessive-compulsive disorder, bulimia and epilepsy in humans or animals. The present invention also relates to the use of the polysaccharide for treating stress, anxiety or depressive behavior, sleep disorders, obsessive-compulsive disorder, bulimia and epilepsy in humans or animals.

12 Claims, No Drawings

USE OF POLYSACCHARIDES FOR TREATING STRESS AND ANXIETY

The present invention relates to the use of a polysaccharide for reducing stress and anxiety in humans or in animals.

The present invention also relates to a composition containing at least one polysaccharide and at least one active agent for treating stress, anxiety or depressive behavior, sleep disorders, obsessive-compulsive disorders, bulimia and epilepsy in humans or animals.

Antidepressants are generally used to treat stress, anxiety or depressive or even suicidal behavior, sleep disorders, obsessive-compulsive disorders and bulimia, and for the therapeutic treatment of chronic pain or epilepsy. Antidepressants are classified into four major families: selective serotonin reuptake inhibitors (SSRIs), tricyclic and tetracyclic antidepressants, monoamine oxidase inhibitors (MAOIs) and atypical antidepressants.

These molecules are generally known for their numerous side effects which are responsible, in the majority of cases, for interruption of the treatment. Among these side effects, mention may in particular be made of somatic and gastrointestinal syndromes, sleep disorders, abnormal movements and behavioral disorders, mental confusion, shaking of the extremities or the risk of causing an epileptic seizure. In addition, these molecules are predominantly known for the addiction that they cause.

In order to reduce the taking of these psychotropic drugs or to completely replace taking them in the least serious cases with a more natural element which does not comprise major risks of dependence or side effects, the present invention relates to a composition comprising at least one polysaccharide and at least one active agent, that can be used in the treatment of stress, anxiety or depressive behavior, sleep disorders, obsessive-compulsive disorders, bulimia and epilepsy in humans or animals.

The present invention is also directed toward the use of said composition for preparing a medicament intended for the prevention or treatment of stress, anxiety or depressive behavior, sleep disorders, obsessive-compulsive disorders, bulimia and epilepsy in humans or animals.

The general term "polysaccharides" is intended to mean polymers formed from a certain number of monosaccharides. Among these polysaccharides, a distinction is made between homopolysaccharides consisting of the same monosaccharide, and heteropolysaccharides formed from different monosaccharides.

The polysaccharide used in accordance with the present invention has:
  between 15 and 50% of 1-6 glucosidic linkages, preferentially between 22% and 45%, more preferentially between 20 and 40%, and even more preferentially between 25 and 35%,
  a reducing sugar content of less than 20%, preferentially between 2 and 20%, more preferentially between 2.5 and 15%, and even more preferentially between 3.5 and 10%,
  a polydispersity index of less than 5, preferentially between 1 and 4, more preferentially between 1.5 and 3, and
  a number-average molecular weight Mn of less than 4500 g/mol, preferentially between 400 and 4500 g/mol, more preferentially between 500 and 3000 g/mol, preferably between 700 and 2800 g/mol, and even more preferentially between 1000 and 2600 g/mol.

The polysaccharide used in accordance with the invention is water-soluble.

It can be prepared according to the process described in patent EP 1 006 128. This patent describes the production of a branched maltodextrin which differs from the standard maltodextrins in particular in terms of the richness thereof in 1→6 glucosidic linkages.

Preferentially, the polysaccharide according to the invention is a modified starch obtained by acid or enzymatic hydrolysis optionally followed by heat treatment. Typically, the polysaccharide is a branched dextrin or a branched maltodextrin.

For the purpose of the invention, the term "branched maltodextrins" is intended to mean maltodextrins of which the 1→6 glucosidic linkage content is greater than that of the standard maltodextrins. Thus, the standard maltodextrins are defined as purified and concentrated mixtures of glucose and of glucose polymers which are essentially 1→4-linked with only from 4 to 5% of 1→6 glucosidic linkages, which have extremely varied molecular weights, which are completely soluble in water and which have a low reducing power.

The standard maltodextrins are conventionally produced by acid or enzymatic hydrolysis of starch. The classification of the standard maltodextrins is based mainly on the measurement of their reducing power, conventionally expressed by the notion of Dextrose Equivalent (DE). With regard to this particular point, the definition of maltodextrins in the Specifications Monograph of the Food Chemical Codex specifies that the D.E. value should not exceed 20.

The D.E. measurement in fact gives only an approximate idea of the average Degree of Polymerization (D.P.) of the mixture of constituent glucose and glucose polymers of standard maltodextrins and therefore of their number-average molecular weight (Mn). In order to complete the characterization of the molecular weight distribution of standard maltodextrins, the determination of another parameter is important, that of the weight-average molecular weight (Mw).

In practice, the Mn and Mw values are measured by various techniques. A method of measurement suitable for glucose polymers, which is based on gel permeation chromatography on chromatography columns calibrated with pullulans of known molecular weights, is for example used.

The Mw/Mn ratio is called the polydispersity index (P.I.) and enables an overall characterization of the molecular weight distribution of a polymeric mixture. As a general rule, the molecular weight distribution of standard maltodextrins results in I.P. values of between 5 and 10.

Patent EP 1 006 128 describes a branched maltodextrin according to the invention obtained by carrying out the following steps:
  a. a dehydrated acidified starch is prepared presenting a moisture content lower than 5%, preferably lower than or equal to 4%,
  b. the acidified starch thus dehydrated is processed in a reactor of the thin-layer type, at a temperature of between 120 and 300° C., preferably between 150 and 200° C.,
  c. the branched starch derivatives thus obtained are collected, purified and preferably concentrated,
  d. said branched starch derivatives are subjected to molecular fractionation according to their number-average molecular weight, in such a way as to obtain the branched maltodextrins.

According to one variant, said polysaccharide has a molecular weight Mw of between 1000 and 6000 g/mol, preferentially between 1500 and 5000 g/mol, and more preferentially between 3000 and 5000 g/mol.

According to one particularity of the invention, said active agent is an antidepressant. Advantageously, the antidepressant is chosen from selective serotonin reuptake inhibitors (SSRIs), tricyclic and tetracyclic antidepressants, monoamine oxidase inhibitors (MAOIs), atypical antidepressants, and mixtures thereof.

Among the suitable active agents, antidepressants of the benzodiazepine or serotonin reuptake inhibitor class are preferred.

These compositions can be formulated for administration to mammals, including humans. The dosage varies according to the treatment and according to the affection in question. These compositions are prepared in such a way as to be able to be administered by the digestive tract, in particular for sublingual, oral or rectal administration. The mixture can be administered in unit administration forms, as a mixture with conventional pharmaceutical supports, to animals or to human beings.

The suitable unit administration forms include oral administration forms such as tablets, gel capsules, powders, granules and oral solutions or suspensions, or syrups, or rectal administration forms such as suppositories.

A preparation in syrup or elixir form can contain at least one polysaccharide combined with the active agent together with a sweetener, an antiseptic, and also a flavoring and a suitable coloring agent.

The water-dispersible powders or granules can contain at least one polysaccharide according to the invention as a mixture with the active ingredient. They can, moreover, contain various agents, alone or as a mixture, such as dispersants, wetting agents, suspension agents, flavor enhancers or sweeteners. These powders can be obtained by atomization or milling and the granules by dry or wet granulation or co-atomization of a mixture according to the invention.

A preparation in tablet form can be optionally followed by a coating step for controlling the release of the mixture according to the invention.

The polysaccharide used according to the invention can be employed in therapy alone, or in combination with at least one other active agent. This other active agent is in particular chosen from active agents suitable for treating anxiety, sleep disorders and epilepsy, or adjuvants for improving the activity of the mixture according to the invention, or else other active agents known for their use in the treatment of said affections. Such active agents are well known to those skilled in the art and are commercially available or else described in reference works.

The invention also relates to the use of a polysaccharide having:
  between 15 and 50% of 1-6 glucosidic linkages,
  a reducing sugar content of less than 20%,
  a polydispersity index of less than 5,
  a number-average molecular weight Mn of less than 4500 g/mol,
for preparing a medicament intended for the treatment of stress, anxiety or depressive behavior, sleep disorders, obsessive-compulsive disorders, bulimia and epilepsy in humans or animals.

The use of polysaccharide in the treatment of anxiety or stress allows the use of a molecule of natural origin without side effects such as addiction.

The invention is directed toward a method for producing a medicament intended for the treatment and/or prevention of stress, anxiety or depressive behavior, sleep disorders, obsessive-compulsive disorders, bulimia and epilepsy in humans or animals, characterized in that a polysaccharide having:
  between 15 and 50% of 1-6 glucosidic linkages,
  a reducing sugar content of less than 20%,
  a polydispersity index of less than 5, and
  a number-average molecular weight Mn of less than 4500 g/mol,
is used alone or as a mixture with at least one active agent for treating stress, anxiety or depressive behavior, sleep disorders, obsessive-compulsive disorders, bulimia and epilepsy in humans or animals.

The polysaccharide is generally administered in daily proportions of from 1 to 100 g, preferentially from 5 g to 50 g and even more preferentially from 8 to 40 g.

The invention also relates to pharmaceutical compositions containing an effective amount of at least one active agent for treating stress, anxiety or depressive behavior, sleep disorders, obsessive-compulsive disorders, bulimia and epilepsy in humans or animals and of at least one polysaccharide defined below, in polysaccharide/active agent ratios of between 500 and 104, preferably between 300 and 105 and even more preferentially between 200 and 106.

The combination of an active agent and of said polysaccharide allows the use of a smaller amount of active agent without, however, reducing the action of the mixture on the symptoms of stress or of anxiety. This mixture can be envisioned during a process in which a treatment is gradually stopped or in cases where the benefit of a drug treatment would be too small compared with the risks of addiction run by the patient.

One embodiment of the invention relates to a kit for therapeutic or prophylactic treatment of the human or animal body, comprising:
  a) a first composition comprising a polysaccharide as defined above; and
  b) a second composition comprising an active agent for treating stress, anxiety or depressive behavior, sleep disorders, obsessive-compulsive disorders, bulimia and epilepsy in humans or animals.

A subject of the invention is also a medicament comprising an effective amount of a polysaccharide having:
  between 15 and 50% of 1-6 glucosidic linkages,
  a reducing sugar content of less than 20%,
  a polydispersity index of less than 5,
  a number-average molecular weight Mn of less than 4500 g/mol,
  and a pharmacologically acceptable vehicle for the treatment of stress, anxiety or depressive behavior, sleep disorders, obsessive-compulsive disorders, bulimia and epilepsy in humans or animals.

Advantageously, the pharmaceutical compositions according to the invention also comprise a suitable pharmaceutical vehicle.

Typically, the invention is directed toward a method for treating and/or preventing stress, anxiety or depressive behavior, sleep disorders, obsessive-compulsive disorders, bulimia and epilepsy in humans or animals, comprising a step of administering, to a patient who needs it, a pharmaceutically effective amount of a polysaccharide having:
  between 15 and 50% of 1-6 glucosidic linkages,
  a reducing sugar content of less than 20%,
  a polydispersity index of less than 5, and
  a number-average molecular weight Mn of less than 4500 g/mol,
said polysaccharide being administered alone or as a mixture with at least one active agent for treating stress, anxiety or depressive behavior, sleep disorders, obsessive-compulsive disorders, bulimia and epilepsy in humans or animals.

According to another aspect of the present invention, the latter also relates to a food supplement suitable for supplementing the diet of individuals prone in particular to anxiety, sleep disorders and epilepsy, containing an effective amount of a polysaccharide according to the invention in combination with food-grade supports of protein or carbohydrate nature.

The invention will now be described in greater detail in the examples hereinafter, based on pharmacobehavioral studies on Wistar rats.

EXAMPLE 1

The effects of an oligosaccharide administered orally at doses of 0.7 and 1.4 g/kg for 14 days were evaluated in a functional observational battery (FOB) in the male Wistar rat. The objective of this FOB test is to evaluate the change in behavioral, neurological and physiological parameters of the rats according to the products tested.

For this, a polysaccharide (PS1) as defined in table 1 is administered by esophageal gavage daily at these two doses for 14 days (6 rats per group). Similarly, a vehicle control consisting of spring water is administered under these conditions. The reference positive control is diazepam: from D0 to D13, methylcellulose is administered to the rats and on D14, diazepam at 3 mg/kg of body weight is also administered.

TABLE 1

|  | PS1 |
| --- | --- |
| Mn (g/mol) | 2640 |
| Mw (g/mol) | 4941 |
| Mn/Mw | 1.9 |
| 1-6 linkages (%) | 29-32 |
| Reducing sugars (%) | 3.9 |

The animals are subjected to the functional observational battery before treatment on D0 and at the end of the study on D14.

Each test comprises three observational phases:
a direct observational phase during which the animal is not disturbed,
an active observational phase during which the animal is handled,
a phase devoted to evaluating the reactions of the animals to reactivity tests.
Several variables are recorded:
Behavioral effects: spontaneous locomotor activity, locomotor behavior disorders, emotionality (vocalization frequency), touch escape reaction, irritability, provoked aggressiveness and freezing behaviors, sleeping/awakening, urination and defecation, sensorimotor responses (visual placing, toe pinch and sound stimulus reaction).
Neurological effects: pupillary response, palpebral reflex, pelvic elevation, tail position, limb and abdominal muscle tone, righting test, grip strength test, suspension test, tremors and piloerection.
Physiological effects: salivation, lacrimation, diarrhea, rectal temperature, heart and respiratory rate.

The results show that, before the first treatment, no significant difference was demonstrated during the first FOB.

After 14 days of administration of the products, significant differences are observed between the rats of the various groups.

| Scores | Vehicle (water) | Reference (diazepam) | PS1 0.7 g/kg | PS1 1.4 g/kg |
| --- | --- | --- | --- | --- |
| Spontaneous activity on D14 | 1.68 | 2.16 | 1.49 | 1.16 |
| p (vs. vehicle) |  | p < 0.10 | NS | p < 0.10 |
| Finger approach reaction on D14 | 0.84 | 0.18 | 0.18 | 0.00 |
| p (vs. vehicle) |  | p < 0.05 | p < 0.05 | p < 0.01 |
| Respiratory rate on D14 | 2.00 | 1.14 | 1.49 | 0.98 |
| p (vs. vehicle) |  | p < 0.01 | p < 0.10 | p < 0.001 |
| Sound stimulus startle reaction on D14 | 1.50 | 0.00 | 0.33 | 0.16 |
| p (vs. vehicle) |  | p < 0.01 | p < 0.05 | p < 0.01 |

Definition of the scores:
Spontaneous activity: 0=excited; 1 to 3 moderate rapid movements; 4: no activity.
Finger approach reaction: 0=none; 1 to 3=slight to strong escape.
Respiratory rate: 0=slow; 1=normal; 2 rapid.
Sound stimulus startle reaction: 0=slight; 1=<1 cm; 2=>1 cm.

In comparison with the vehicle on D14:
Spontaneous activity: The Mann-Whitney test shows that the rats of the reference group tend to be significantly less active, whereas the rats of the PS1 0.7 g/kg group and the PS1 1.4 g/kg group tend to be significantly more active. For the PS1 group, the rats show a greater interest in their surroundings.
Finger approach reaction: The Mann-Whitney test shows that the rats of the reference group and of the PS1 at 0.7 g/kg group and the PS1 at 1.4 g/kg group are significantly less reactive to a finger approach. In addition, these rats are calmer, less anxious.
Respiratory rate: The Mann-Whitney test shows that the rats of the reference group and the PS1 at 1.4 g/kg group exhibit respiratory rates, but also heart rates, that are significantly slower. For the PS1 groups, the rats are calmer.
Sound stimulus startle reaction: The Mann-Whitney test shows that the rats of all the groups display startling to a significantly lesser degree. The rats of the PS1 groups are calmer.
In comparison with the reference on D14:
Spontaneous activity: The Mann-Whitney test shows that the rats of the PS1 at 0.7 g/kg group and the PS1 at 1.4 g/kg group are significantly more active.
Finger approach reaction: The Mann-Whitney test does not show any difference.
Respiratory rate: The Mann-Whitney test does not show any difference.
Sound stimulus startle reaction: The Mann-Whitney test does not show any difference.

In conclusion, the set of parameters studied shows that the rats of the groups treated with PS1, at the two doses, were less anxious and more curious after 14 days of treatment.

Furthermore, for a certain number of criteria, the treatment with the PS1 polysaccharides shows the same effects as the treatment with diazepam.

EXAMPLE 2

The anti-stress effects of a PS1 polysaccharide administered orally for eleven days were evaluated in the male Wistar rat in a righting test.

For this, the PS1 is administered by esophageal gavage daily at the doses of 0.7, 1.4 and 2.8 g/kg of body weight for eleven days (16 rats per group). Similarly, a vehicle control represented by spring water is administered under these conditions.

The rats undergo a righting test daily from D1 to D11. This test consists in placing the rat on the palm of the hand, on its back, and evaluating the speed at which it rights itself. A percentage of slow righting is calculated per group of rats for the treatment period of from D1 to D11 after a score of 0=rapid righting or 1=slow righting has been attributed.

The results obtained are given in the table below. They are expressed as % number of rats righting themselves more slowly between D1 and D11.

|  | Vehicle (water) | PS1/0.7 g/kg | PS1/ 1.4 g/kg | PS1/ 2.8 g/kg |
|---|---|---|---|---|
| Righting on D0 | 0.00 ± 0.00 | 0.00 ± 0.00 | 0.00 ± 0.00 | 0.00 ± 0.00 |
| Righting between D1 and D11 | 17.71 ± 7.94 | 41.67 ± 8.63 | 36.46 ± 6.67 | 24.48 ± 6.61 |

There is a phenomenon of the animals growing accustomed over time: the percentage of rats righting themselves slowly goes from 0% to 17% for the vehicle control batch (water). On the other hand, this percentage doubles for the PS1 at 0.7 g and PS1 at 1.4 g batches and reaches approximately 36 to 41%. The animals are therefore less stressed to find themselves in this position.

EXAMPLE 3

The anti-stress effects of a PS1 polysaccharide, administered orally for 14 days, were evaluated in the male Wistar rat in the Conditioned Defensive Burying (CDB) test.

For this, the PS1 is administered by esophageal gavage daily at the doses of 0.7, 1.4 and 2.8 g/kg of body weight for 14 days (8 rats per group). Similarly, a vehicle control represented by spring water is administered under the same conditions. The reference positive control is diazepam: from D0 to D13, methylcellulose is administered to the rats, and on D14, diazepam at 1 mg/kg or 3 mg/kg of body weight is administered to the rats. The PS1 and diazepam mixture is also studied: the PS1 is administered for 14 days alone, and on D14, diazepam at 1 mg/kg is added to the esophageal gavage of the PS1.

On D14, the rats are subjected to the Conditioned Defensive Burying (CDB) test. For this, an electric probe is inserted into a cage before the start of the test. Each rat is placed in the experimental device on the opposite side to the probe and a single electric shock, of weak intensity (2 mA), is delivered to the animal at the moment it places its front paw on the probe for the first time. Following the shock, the behavior of the rat is recorded for five minutes; an overall stress score is attributed for each rat. The greater the stress, the higher the score.

The results obtained are given in the table below.

The statistical results show that the overall stress scores for the rats of the 3 mg/kg diazepam group and the 2.8 g/kg PS1+1 mg/kg diazepam group are significantly lower than that of the vehicle group.

The scores of the PS1 at 1.4 g/kg group and the 1 mg/kg diazepam group tend to be lower than that of the vehicle group.

The scores of the PS1 at 0.7 g/kg group and the PS1 at 2.8 g/kg group are not significantly different than that of the vehicle group, although the scores are lower for these two batches.

It is possible to conclude that:
the intermediate dose of PS1 at 1.4 g/kg gives an interesting result regarding the stress score;
the effects observed for the PS1 and diazepam batches are significantly identical;
individually, the scores of the diazepam at 1 mg/kg group and the PS1 at 2.8 g/kg group are respectively 92 and 107. When these two products are combined, the overall score decreases to 75. The PS1 potentiates the effects of the diazepam. This synergy would make it possible to limit the doses of diazepam administered and to limit the side effects thereof. The consumption of PS1 goes toward an optimization of the effect of a medicament.

The invention claimed is:

1. A composition comprising at least one polysaccharide as an active agent and at least one additional active agent for treating stress, anxiety or depressive behavior, sleep disorders, obsessive-compulsive disorders, bulimia and epilepsy in humans or animals, said polysaccharide having:
   between 15 and 50% of 1-6 glucosidic linkages,
   a reducing sugar content of less than 20%,
   a polydispersity index of less than 5, and
   a number-average molecular weight Mn of less than 4500 g/mol.

2. The composition as claimed in claim 1, wherein said polysaccharide has:
   between 20% and 40% of 1-6 glucosidic linkages,
   a reducing sugar content of between 2 and 20%,
   a polydispersity index of between 1 and 4, and
   a number-average molecular weight Mn of between 500 and 3000 g/mol.

3. The composition as claimed in claim 1, wherein the polysaccharide has a molecular weight Mw of between 1000 and 6000 g/mol.

4. The composition as claimed in claim 1, wherein said at least one additional active agent is an antidepressant.

5. The composition as claimed in claim 4, wherein said at least one additional active agent is selected from the group consisting of selective serotonin reuptake inhibitors (SSRIs), tricyclic and tetracyclic antidepressants, monoamine oxidase inhibitors (MAOIs), atypical antidepressants, and mixtures thereof.

6. The composition as claimed in claim 1, wherein said composition is in sublingual, oral or rectal administration form.

|  | Vehicle (water) | PS1/0.7 g/kg | PS1/1.4 g/kg | PS1/2.8 g/kg | Diazepam reference 3 mg/kg | Diazepam reference 1 mg/kg | PS1 2.8 g/kg + Diazepam 1 mg/kg |
|---|---|---|---|---|---|---|---|
| Mean ± SEM | 121.94 ± 14.70 | 117.06 ± 17.06 | 90.50 ± 17.17 | 107.63 ± 12.43 | 65.25 ± 7.15 | 92.57 ± 17.99 | 75.36 ± 12.72 |
| p (vs vehicle) | — | NS | Tendency | NS | p < 0.01 | Tendency | p < 0.05 |

7. The composition as claimed in claim 6, wherein said composition is in the form of tablets, gel capsules, powders, granules, oral solutions or suspensions, emulsions, syrups or suppositories.

8. The composition as claimed in claim 3, wherein the polysaccharide has a molecular weight Mw of between 1500 and 5000 g/mol.

9. The composition as claimed in claim 3, wherein the polysaccharide has a molecular weight Mw of between 3000 and 5000 g/mol.

10. A method for treating stress, anxiety or depressive behavior, sleep disorders, obsessive-compulsive disorders, bulimia and epilepsy in humans or animals, comprising:
   administering to a human or animal in need thereof a medicament comprising:
   1 to 100 g of a polysaccharide having:
   between 15 and 50% of 1-6 glucosidic linkages,
   a reducing sugar content of less than 20%,
   a polydispersity index of less than 5,
   a number-average molecular weight Mn of less than 4500 g/mol,
   and a pharmacologically acceptable vehicle,
   said medicament being in a form selected from the group consisting of tablets, gel capsules, powders, granules, oral solutions or suspensions, emulsions, syrups and suppositories,
   said 1 to 100 g being an effective amount for the treatment of stress, anxiety or depressive behavior, sleep disorders, obsessive-compulsive disorders, bulimia and epilepsy in humans or animals.

11. A method for treating stress, anxiety or depressive behavior, sleep disorders, obsessive-compulsive disorders, bulimia and epilepsy in humans or animals comprising:
   administering to a human or animal in need thereof a composition comprising an effective amount of at least one polysaccharide as an active agent and at least one additional active agent for treating stress, anxiety or depressive behavior, sleep disorders, obsessive-compulsive disorders, bulimia and epilepsy in humans or animals, said polysaccharide having:
   between 15 and 50% of 1-6 glucosidic linkages,
   a reducing sugar content of less than 20%,
   a polydispersity index of less than 5, and
   a number-average molecular weight Mn of less than 4500 g/mol.

12. A kit for therapeutic or prophylactic treatment of the human or animal body, comprising:
   a) a first composition comprising a polysaccharide having:
   between 15 and 50% of 1-6 glucosidic linkages,
   a reducing sugar content of less than 20%,
   a polydispersity index of less than 5,
   a number-average molecular weight Mn of less than 4500 g/mol; and
   b) a second composition comprising an active agent for treating stress, anxiety or depressive behavior, sleep disorders, obsessive-compulsive disorders, bulimia and epilepsy in humans or animals.

* * * * *